United States Patent [19]
Osborn, III et al.

[11] Patent Number: 6,095,998
[45] Date of Patent: Aug. 1, 2000

[54] EXPANDABLE BAG TAMPON AND SPREADING TAMPON APPLICATOR THEREFOR

[75] Inventors: Thomas Ward Osborn, III; Richard Tweddell, III; Lisa Ann MacKay, all of Cincinnati, Ohio

[73] Assignee: The Procter & Gamble Company, Cincinnati, Ohio

[21] Appl. No.: 09/124,351

[22] Filed: Jul. 29, 1998

[51] Int. Cl.[7] ..................................................... A61F 13/20
[52] U.S. Cl. ................................ 604/11; 604/14; 604/15; 604/904
[58] Field of Search ................................ 604/904, 11–18, 604/59, 57, 1–3, 363, 285–288

[56] References Cited

U.S. PATENT DOCUMENTS

| | | |
|---|---|---|
| 61,417 | 2/1867 | Grant . |
| 1,969,671 | 8/1934 | Nelson . |
| 2,458,685 | 1/1949 | Crockford . |
| 2,733,714 | 2/1956 | Haas . |
| 2,884,925 | 5/1959 | Meynier, Jr. . |
| 3,068,867 | 12/1962 | Bletzinger et al. . |
| 3,495,586 | 2/1970 | Regenbogen . |
| 3,706,311 | 12/1972 | Kokx et al. . |
| 3,749,094 | 7/1973 | Duncan . |
| 3,753,437 | 8/1973 | Hood et al. . |
| 3,762,413 | 10/1973 | Hanke . |
| 3,857,395 | 12/1974 | Johnson et al. ............... 604/904 |
| 3,885,563 | 5/1975 | Johnson et al. ............... 604/11 |
| 3,971,398 | 7/1976 | Krantz . |
| 3,981,305 | 9/1976 | Ring ............................ 604/904 |
| 3,986,511 | 10/1976 | Olofsson et al. . |
| 4,010,751 | 3/1977 | Ring ............................ 604/15 |
| 4,211,225 | 7/1980 | Sibalis . |
| 4,536,178 | 8/1985 | Lichstein et al. . |
| 5,346,468 | 9/1994 | Campion et al. . |
| 5,370,633 | 12/1994 | Villata . |
| 5,395,383 | 3/1995 | Adams et al. ................. 604/14 |
| 5,558,631 | 9/1996 | Campion et al. . |
| 5,659,934 | 8/1997 | Jessup et al. . |

*Primary Examiner*—John G. Weiss
*Assistant Examiner*—Dennis Ruhl
*Attorney, Agent, or Firm*—Jeffrey V. Bamber; Matthew P. Fitzpatrick

[57] ABSTRACT

An expandable bag catamenial tampon and spreading tampon applicators for such a tampon are disclosed. The catamenial tampon is in the form of a soft, conformable, hollow bag. The applicator is capable of inserting the tampon into the vaginal tract and spreading the tampon open within the vaginal cavity. The applicator has an applicator element with a leading end and a trailing end. The bag-like tampon is placed over the leading end of the applicator when the tampon is in a flaccid initial configuration which defines an initial width, and the applicator is used to spread the tampon to a greater deployed width. In one embodiment, the applicator comprises tube having an interior and a flexible material which has one end that is formed into a flexible and expandable loop. The flexible loop is slidably mounted within the tube. The flexible loop is contained inside the tube until it is desired to deploy the tampon. When it is desired to deploy the tampon, the flexible loop with the tampon thereon is pushed out the expulsion end of the tube. The flexible loop expands laterally and spreads the tampon open within the vaginal cavity.

7 Claims, 5 Drawing Sheets

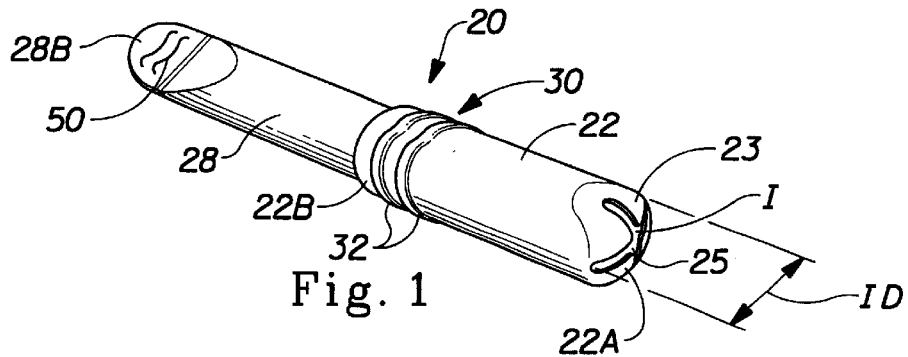
Fig. 1
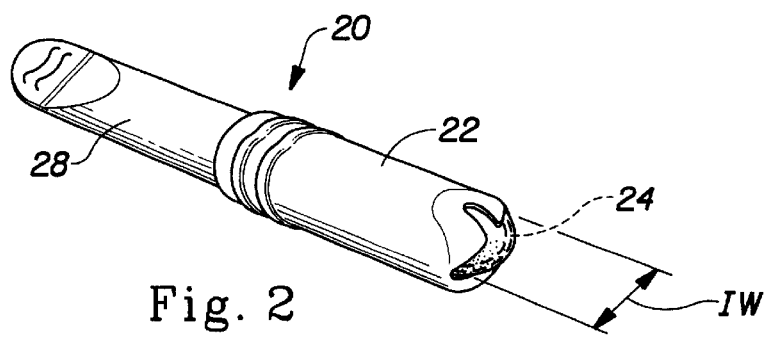
Fig. 2
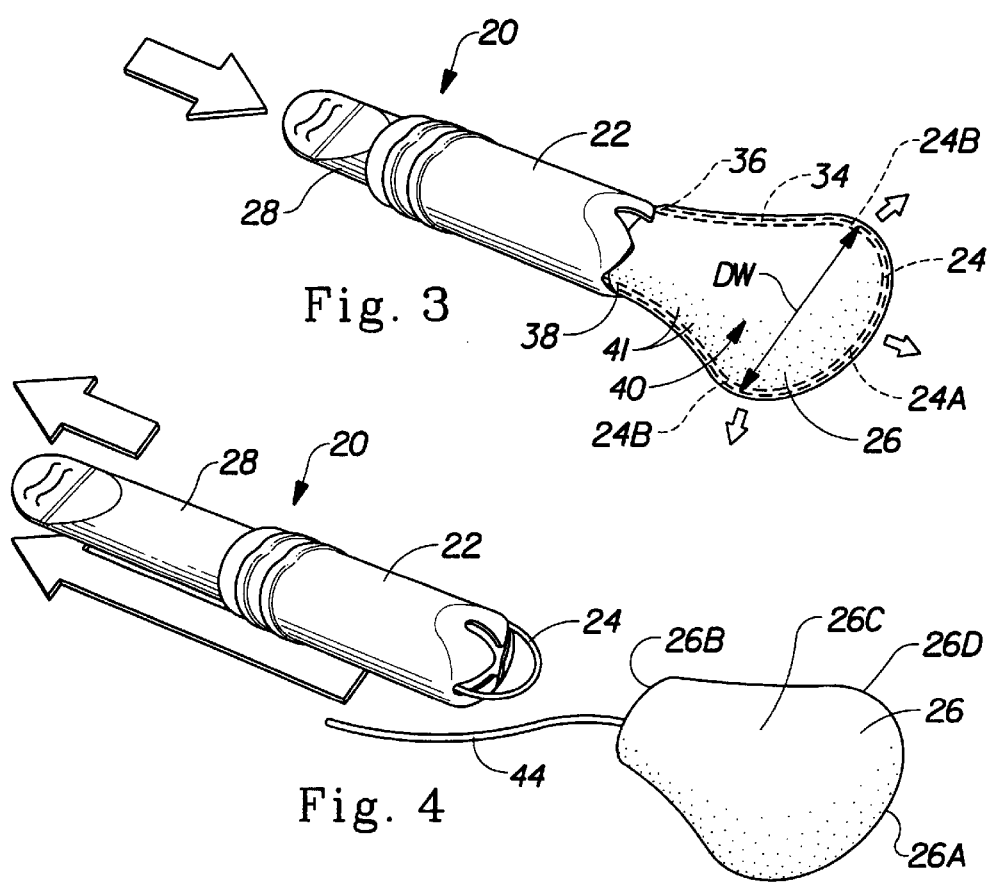
Fig. 3
Fig. 4

EXPANDABLE BAG TAMPON AND SPREADING TAMPON APPLICATOR THEREFOR

FIELD OF THE INVENTION

This invention relates to applicators for catamenial tampons, and more particularly to an applicator which is capable of inserting a tampon into the vaginal tract and spreading the tampon open within the vaginal cavity.

BACKGROUND OF THE INVENTION

It has been long recognized that the internal vaginal cavity in its normal collapsed state is of much wider dimension in its transverse plane than in its vertical plane. It is equally well known that the minimum dimension of the vagina is at the introitus while the maximum dimension is near the cervix. It is desirable therefore, when considering a tampon for catamenial use, to provide a structure which is in its initial state is of a size small enough to pass through the vaginal orifice without discomfort, and when once inside the vaginal cavity and beyond the restrictions of the orifice may be expanded, particularly in the lateral direction, to contact substantially all of surface of the vaginal walls from one side to the other in the vaginal cavity to prevent early bypass of the menstrual discharges from the cervix. Since the vaginal wall in its normal collapsed state is flaccid and has multiple folds and wrinkles which provide channels through which a significant portion of the menstrual fluids normally flow, it is also important that the absorbent tampon be as soft and conformable as possible, in order to conform to shape of the vaginal cavity and fit within these channels to minimize leakage.

The absorbent catamenial tampons now in general use comprise small, highly compressed, cylindrical plugs about three-eighths to one-half inch (about 1.0 cm to 1.3 cm) in diameter and from 1½ to 2½ inches in length (about 3.8 cm to 6.4 cm). Because of the need for absorbent capacity, they are usually formed from batts much larger in size than the vaginal orifice, and compressed to the small size indicated above in order to facilitate insertion. As fluid is absorbed, these compressed tampons are expected to expand (or re-expand) toward their original precompressed size, and to eventually become large enough to effectively block the vaginal cavity against fluid leakage or bypass. While it has been found that these compressed tampons perform their intended function tolerably well, even the best of them do not expand sufficiently, or fast enough, to provide a good transverse block against leakage even though the vertical block may be satisfactory. Further, most of these tampons generally use only a portion of their absorptive capacity before leakage. Since these tampons rely on some fluid absorption to expand, it is clear that fluid bypass and leakage can occur prematurely.

Numerous attempts have been made to solve this problem. Some approaches in the patent art suggest a tampon with a built-in mechanical expansion means, a typical example being U.S. Pat. No. 3,706,311 to Kokx et al. However, while a good transverse block appears to be produced, the mechanical expansion means disclosed in that patent is in the form of a flat spring-like element which after insertion permanently maintains the spread configuration of the tampon, may make it difficult to remove.

Another approach is described in U.S. Pat. No. 3,512,528 to Whitehead et al, which teaches the use of a sack of absorbent material collapsed to a small size for insertion and which after insertion is expanded by the introduction of a gas or a fluid internally of the sack. The multiple steps and complicated manipulation of the gas or fluid introduction means required when using this type of tampon detract from what otherwise appears to be an effective solution of the problem.

Still another approach is described in U.S. Pat. No. 3,857,395 issued to Johnson, et al. The Johnson, et al. patent teaches the use of an elongated inserter device over which a flat tampon is draped. The inserter is said to permit the draped portion of the tampon to be pulled, rather than pushed into the cavity from the point at which the tampon is supported on the leading end of the inserter. The inserter means is equipped with a bilateral expansion mechanism which at the user's option may be operated to transversely spread the tampon at the time of insertion. The inserter device described in the Johnson, et al. patent suffers from many drawbacks, however. The Johnson inserter device is a complicated device comprising a pair of hinged arms that are capable of laterally diverging at a hinge or joint. The angular nature of the hinged arms would appear to make that inserter uncomfortable to use. The complex nature of the hinged arms would also appear to make it difficult and expensive to manufacture. As a result, it would not be suitable as a disposable applicator.

Another problem that exists in deploying tampons having a greater transverse dimension within the vaginal cavity is that this greater transverse dimension of the vaginal cavity is roughly perpendicular to the vaginal opening.

One attempt to address this latter problem is described in U.S. Pat. No. 3,068,867 issued to Bletzinger, et al. The Bletzinger, et al. patent is directed to a tampon insertion device having a positioning indicator thereon. The device described in the Bletzinger, et al. patent comprises an insertion device for tampons which are either of cylindrical cross-section, or non-cylindrical cross-section but constructed to expand when subjected to fluids in a non-cylindrical shape. The insertion device is provided with an indicator that aids the user in inserting the tampon with its major cross-sectional axis transverse to the major axis of the vaginal opening.

The Bletzinger device, however, is awkward in that it requires insertion of the widest dimension of the tampon cross-wise to the narrowest dimension of the vaginal opening. Thus, a need exists for a tampon applicator which is capable of effectively deploying a tampon having a non-cylindrical shape in the vaginal cavity which does not require alignment of the widest dimension of the tampon cross-wise to the narrowest dimension of the vaginal opening.

SUMMARY OF THE INVENTION

This invention relates to applicators for catamenial tampons, and more particularly to an applicator which is capable of inserting a tampon into the vaginal tract and spreading the tampon open within the vaginal cavity. The present invention is also directed to the combination of an expandable catamenial tampon and a spreading tampon applicator.

The spreading tampon applicator is preferably capable of first inserting and then bilaterally spreading the tampon to a partially or fully-opened condition within the vaginal cavity. The tampon applicator comprises an applicator element with a leading end and a trailing end. In embodiments that are less preferred from a convenience standpoint, the inserter may comprise a rod or other structure that is used for inserting the tampon and the inserter is manually moved from side to side to deploy the tampon. In embodiments that are more preferred for convenience, the applicator includes a structure that expands the tampon without such action on the part of the user.

In such more convenient embodiments, the spreading tampon applicator preferably comprises a holder in the form of an elongate tube having insertion end, a gripping end, an interior, and an inside diameter. The spreading tampon applicator preferably further comprises at least one flexible, movable structure that is adapted to reside inside the tubular holder until it is pushed out the insertion end. The flexible, movable structure preferably has resilient opposed portions that are biased to expand when not subject to confinement in the tubular holder. A hollow "bag-like" tampon is preferably placed over the flexible structure when the flexible structure is inside the tubular holder. When the flexible structure is pushed out of the insertion end of the holder it spreads out to deploy the tampon. The flexible, movable structure can comprise one or more elements. These elements preferably have opposing portions that are capable of flexing and expanding away from each other. In preferred embodiments, the elements are convexly rounded to provide a comfortable surface against the wearer's body.

In one preferred embodiment, the flexible, movable structure comprises at least one flexible loop of material. The loop of material preferably comprises an elongate piece of material, preferably in the form of a flexible rod, which has two ends. In a preferred embodiment, the flexible rod is bent so that one portion of the piece of material is formed into an expandable loop and the ends of the piece of material opposite the loop extend in the same general direction as one another. The loop is preferably slidably mounted within the tubular holder. The "bag-like" tampon is preferably placed over the flexible loop. The loop has an initial width which is less than or equal to the inside diameter of the tubular holder, and is expandable so that it has a deployed width which is greater than the inside diameter of the tubular holder.

The spreading tampon applicator described herein is small enough in size to pass through the vaginal orifice without undue stretching or friction. Once the flexible loop is inside the vaginal cavity, it expands the tampon in the lateral direction and positions the tampon in the proper orientation in the vaginal cavity. In all of the embodiments described herein, the spreading force that is exerted by the applicator can be regulated by the force applied by the wearer on the applicator. The spreading tampon applicator of the present invention, unlike prior angular and hinged devices, is very comfortable to use, simple and cost-effective to make.

A non-limiting number of embodiments of the present invention are possible. In the most basic form of the loop-type of embodiment, the applicator comprises a single loop of material (and such an embodiment can even be used alone without the tubular holder). In one particularly preferred embodiment, the applicator comprises two (or more) loops of material. Such a particularly preferred embodiment may be used with or without a tubular holder. Preferably, it is used in conjunction with a tubular holder. In this particularly preferred embodiment, the loops of material are preferably oriented at an angle of about 90 degrees relative to each other when the applicator is viewed from the end. This embodiment has the advantage of providing an increased likelihood of ensuring that one of the loops of material will be oriented in the same plane as the vaginal cavity. In another embodiment, the loop can be provided with the ability to rotate as it deploys. Such an embodiment is useful in initially aligning the loop parallel to the opening of the vagina when the tampon is inserted through the vaginal opening, and then changing the orientation of the loop so that it is aligned parallel to the vaginal cavity when the tampon is deployed. In still another embodiment, the applicator has a loop that is constrained in length as it deploys by joining a portion of the loop to the inserter. The loop in this embodiment resembles a "ram's horn" in appearance.

Other embodiments are also possible. For example, the flexible, movable structure need not be in the form of a loop. It can, for instance, instead be comprised of separate prongs that are biased to flex away from each other, and spread out. Numerous other embodiments are possible. Many of the embodiments described herein are particularly useful because they provide a "signal" to the user that the tampon is properly oriented and is spread laterally across the vaginal cavity. The applicators described herein are also capable of deploying a tampon which closely fits the cross-section of the vaginal cavity. In particular, the applicators described herein may be suitable for fitting the tampon to the portion(s) of the vaginal cavity which have a cross-section that resembles a compressed upper case letter "H".

BRIEF DESCRIPTION OF THE DRAWINGS

FIG. 1 is a perspective view of one embodiment of a tampon applicator according to the present invention.

FIG. 2 is a perspective view of the tampon applicator shown in FIG. 1 with the loop partially deployed.

FIG. 3 is a perspective view of the tampon applicator shown in FIG. 1 with the flexible loop fully deployed.

FIG. 4 is a perspective view of the tampon applicator shown in FIG. 1 with the loop retracted.

DETAILED DESCRIPTION OF THE INVENTION

Figure 5:
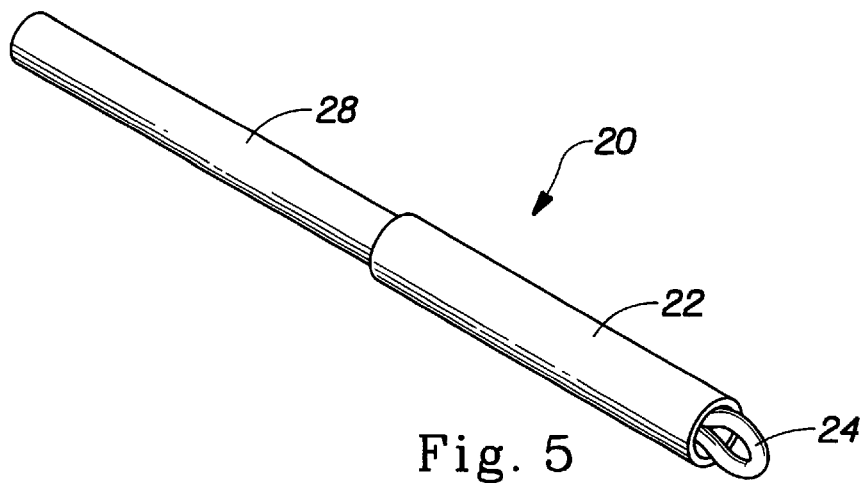
FIG. 5 is a perspective view of another alternative embodiment of the tampon applicator of the present invention in which the flexible loop is provided with the ability to rotate 90 degrees during deployment to accommodate the difference in orientation between the vaginal opening and the vaginal cavity.

This invention relates to applicators for catamenial tampons, and more particularly to applicators which are capable of inserting a tampon into the vaginal tract and spreading the tampon open within the vaginal cavity. The present invention also relates to a combination of an improved conformable tampon and a spreading applicator therefor to be used for inserting and spreading the tampon open within the vaginal cavity.

FIG. 1 shows one embodiment of the tampon applicator 20 of the present invention. The applicator 20 shown in FIG. 1 is an example of a simplified version of one embodiment of the present invention. The tampon applicator 20 shown in FIG. 1 generally comprises a holder in the form of a tube, preferably an elongate tube 22 and at least one flexible, movable structure that is adapted to reside inside the tube 22 until it is pushed out the end of the tube. In the embodiment shown in FIG. 1, the flexible, movable structure comprises flexible loop 24. The flexible loop 24 comprises the applicator element in such an embodiment. The tampon 26, one embodiment of which is shown in FIGS. 3 and 4, fits over the loop 24 and is capable of expanding when the loop 24 expands. As shown in FIG. 1, the tampon applicator 20 preferably also includes a plunger 28 for expelling the tampon 26. The plunger 28 is telescopically and slidably mounted inside the tubular holder 22. The applicator 20 is preferably inexpensive enough to manufacture that it can be disposable after a single use, although it is also possible for the applicator 20 to be reusable. The components of this embodiment of the tampon applicator of the present invention will now be looked at in greater detail.

The holder 22 is preferably an elongate hollow tube that has insertion end (or "expulsion end") 22A, a gripping end 22B, an interior I, and an inside diameter ID. The holder 22 can be of either the open end type, or the closed end type. The holder 22 can be constructed similarly to tubular holders of the type used in tampon applicators currently in use. Examples of such a tubular holder are described in U.S. Pat. No. 5,346,468 issued to Campion, et al. on Sep. 13, 1994, and U.S. Pat. No. 5,558,631 issued to Campion, et al. on Sep. 24, 1996. The holder 22 can be of any suitable cross-sectional shape. Suitable cross-sectional shapes include, but are not limited to circular, oval, flattened circular, and elliptical. Preferably, the holder 22 has a circular cross-sectional configuration. If the holder 22 is of a closed end type, the "petals" 23 that define the opening 25 at the insertion end 22A can be of any conventional type. It has been found that it is not necessary to modify the shape of the opening 25 at the insertion end 22A to permit the flexible loop 24 to be pushed through the opening, since the petals 23 are sufficiently flexible to move out of the way of the flexible loop 24. In the embodiment shown in the drawings, the opening 25 has a cruciform shape.

In the embodiment shown in FIG. 1, the tubular holder 22 comprises an optional finger grip 30 for assisting the user in holding the tubular holder 22 when inserting the tampon, and pushing the plunger 28. The tubular holder 22 may or may not be provided with such an optional fingergrip 30 to assist the user in inserting the tampon 26. The finger grip 30, if used, can be in any suitable form, including, but not limited to raised formations, depressions, and apertures. In the embodiment shown in FIG. 1, the finger grip 30 comprises a pair of embossed rings 32.

The flexible, movable structure 24 can comprise any suitable type of flexible, expandable, and preferably rounded element that is capable of remaining in the holder 22 until it is desired to deploy the tampon. When the time to deploy the tampon 26 arises, the flexible, movable structure 24 is capable of moving within the holder 22 (hence it is movable) and expanding to spread the tampon 26 within the vaginal cavity. Thus, the tampon applicators described herein, plus any variations of the same that will become apparent to one of ordinary skill in the art after reading this specification, may be described as comprising a means for expanding the tampon across the vagina.

The flexible, movable structure 24 is preferably in the form of a loop so that it is most comfortable when it is deployed. The flexible, movable structure 24 preferably has a relatively low force of expansion (force which it applies to objects in contact with it when it opens) so that it minimizes any distortion of the vaginal opening when the tampon 26 is inserted through the vaginal opening, and minimizes the distortion of the vaginal cavity when the tampon 26 is deployed within the vaginal cavity. The flexible, movable structure 24 preferably only distorts the vaginal cavity to the extent necessary to properly deploy the tampon 26 therein. The flexible, movable structure 24 is also capable of flexing to adjust to the shape of the vaginal cavity. This can be contrasted with devices that use structures employing hinged arms in order to expand.

The flexible loop 24 preferably comprises an elongate piece of material 34 such as a flexible rod or tube, having two ends 36 and 38 that extend in the same general direction. The flexible loop 24 may also be referred to herein as a "wisk" since it resembles a wisk of the type used for cooking (e.g., for beating eggs). (However, the loops on such a cooking implement are typically not flexible and expandable). The piece of material 34 that comprises the flexible loop has one portion which is formed into the flexible and expandable loop 24. The flexible loop is advantageous in that all of the portions that will come into contact with the wearer's body are preferably convexly rounded to provide a comfortable structure for contacting the wearer's body, in contrast to prior devices having angular hinge-type mechanisms. However, it is also possible to modify the flexible loop 24 to provide one or more portions thereof with one or more segments along its length that are concavely rounded, rectilinear, or both.

Thus, not only is the leading end 24A of the flexible loop 24 convexly rounded, but the longitudinal sides 24B of the flexible loop 24 are also preferably convexly rounded. In some embodiments, the entirety of the longitudinal sides 24B of the flexible loop 24 is convexly rounded. The fact that the longitudinal sides 24B are convexly rounded causes them to be biased outward away from each other when the flexible loop 24 is constrained in width, such as when it resides in the holder 22. As a result, the flexible loop 24 expands on its own when it is pushed out of the end of the holder 22, and no mechanical mechanism is required to be present in the applicator 20 to spread the flexible loop 24.

The piece of material 34 that is formed into the flexible loop 24 can comprise any suitable material that has the characteristics described herein. The piece of material (or rod) 34 can have any suitable cross-sectional shape. Preferably, it has a round cross-sectional shape. The piece of material 34 should preferably be very comfortable when it comes in contact with the delicate parts of the user's body. The piece of material 34 is preferably resiliently elastomeric so that it does not undergo "set" when it is within the holder 22 and can expand when outside the holder 22. The piece of material 34 should preferably be substantially non-creeping. Preferred materials for the piece of material 34 typically comprise some type of elastomeric material including rubber, such as natural rubber, latex, nitrile, and silicone rubbers. Other materials that can be formed into structures with spring-like properties, such as a metal diaphragm spring material may also be used. Such other materials may optionally be coated with another material for improved comfort. Suitable coatings include, but are not limited to any of the foregoing rubber materials.

The flexible loop 24 is movable within the tubular holder 22, and is preferably slidably mounted within the tubular holder 22. The flexible loop 24 has an initial width, IW, which is less than or equal to the inside diameter, ID, of the tubular holder 22, and a deployed width, DW, shown in FIG. 3, which is greater than the inside diameter, ID, of the tubular holder 22. That is, the flexible loop 24 expands from a first transverse width to a second transverse width. In one non-limiting example, the flexible loop 24 may have an initial width, IW, of about 7/16 inch (about 1 cm) and a deployed width, DW, of about 1 inch (about 25 cm) to about 1¼ inches (about 30 cm to about 35 cm).

The tampon 26 can be of any suitable configuration that is able to be expanded upon insertion into the vaginal cavity by the spreading tampon applicator 20 of the present invention. The tampon 26 is preferably conformable to the shape of the user's vaginal cavity. It is also preferably soft and substantially uncompressed, and does not rely on expansion from a compressed state in order to fit and fill the vaginal cavity.

One embodiment of the tampon 26 is shown in the FIG. 3. The tampon 26 fits over the flexible loop 24 and is capable of expanding bi-laterally when the loop 24 expands. In the embodiment of the tampon shown in FIG. 3, the tampon 26 comprises an absorbent element that has a configuration that resembles an "oven mitt" used in cooking. The tampon 26 has a head 26A or end that is the first portion of the tampon to be inserted into the vaginal cavity, a trailing end 26B, surfaces 26C, and edges 26D. The tampon 26 has a structure that resembles a bag (that is, it is "bag-like") in that it preferably has an open trailing end 26B, and a hollow, rather than a solid interior. Thus, the tampon 26 preferably has two or more sides 26C that are joined together, a closed end 26A, and an open end 26B. (However, it is also possible to insert a variety of different types of optional elements (absorbent or otherwise) into the interior of the tampon 26 so that the bag-like structure may contain another element and, thus, will not be completely empty.)

The tampon 26 is preferably highly flaccid and conformable. The tampon 26 need not be, and preferably is not pre-compressed to a point where the fibers (or other components comprising the material of the tampon) "set" and re-expand upon the absorption of liquids. The tampon 26, therefore, need not rely on resilience or "spring" within the fibers of the tampon itself to re-expand. This feature allows the tampon 26 to be significantly more flaccid and conformable than previous tampons and, consequently, more comfortable than such devices.

The tampon 26 may have a number of suitable plan view shapes. Suitable plan view shapes, include, but are not limited to: generally rectangular with rounded edges, a shape like the portion of a sock that is worn on a wearer's foot (that is, not including the portion angled away from such a portion, that is worn over the wearer's ankle), generally trapezoidal, or as shown in FIG. 3, a shape that resembles a flattened light bulb or flattened hot air balloon. Thus, the tampon 26 may be wider at the head 26A; wider at the trailing end 26B; or approximately equal width from the head 26A to the trailing end; or, widest at some point between the head 26A and the trailing end 26B. The tampon 26 can be of any suitable size. In one embodiment, the tampon 26 has a length measured from the head 26A to trailing end 26B of about 2½ inches (about 6 to about 6.5 cm) and a width measured from one side 26D to the other of between about 25 mm to about 30 or 35 mm plus or minus about 3 mm.

The tampon 26 can have a variety of different cross-sectional shapes when it is placed over the flexible loop 24 prior to deploying the tampon 26. For example, it may have a generally flat cross-section (e.g., one that might resemble an oval) that fits closely over the loop 24, it may have a generally circular cross-section, or a generally rectangular cross-section. In other embodiments, the tampon 26 may have a modified cross-section, such as the one shown in FIG. 15 that has two of its sides pleated so that it resembles a paper shopping bag when looking into the open end of the tampon 26. The pleats will allow the sides of the tampon 26 to expand laterally. In a variation of such an embodiment, the pleats may be provided in an accordion-like fashion across the (top and bottom) surfaces 26C so that the tampon is provided with increased ability to expand laterally. In another variation of such an embodiment, it may be desirable for the tampon 26 to have a plurality of such pleats disposed around its cross-section that are capable opening in any desired direction (that is, in three dimensions).

The tampon 26 preferably has a generally flat configuration when deployed. This allows it to conform to the shape of the vaginal cavity. (The shape of the vaginal cavity is described in greater detail in U.S. Pat. No. 3,749,094 issued to Duncan on Jul. 31, 1973.)

The outside surface 40 of the tampon 26 can be plain, or it can be textured. Preferably, it is textured. Although the texture of the tampon 26 is not shown in great detail in the drawings for simplicity of illustration, the tampon 26 preferably has an outside surface 40 that comprises a plush or terry cloth type fabric. The outside surface 40 preferably has a plurality fibers or other elements 41 extending outwardly therefrom (preferably generally perpendicular to the surfaces of the expanded tampon 26). This is in contrast to current tampons in which the fibers comprising such tampons generally lay flat relative to the surface of the expanded tampon. The fibers or elements 41 of the tampon 26 described herein can, as a result, penetrate into the rugosities in the vaginal cavity to intercept menses and reduce "bypass" failures (failures from menses traveling in these rugosities and around the tampon).

The tampon 26 can be made of any suitable material. Suitable materials include cotton, rayon, and blends of cotton and rayon. The materials for the tampon 26 can be formed into a fabric that is suitable for use in the tampon 26 by any suitable process. Suitable types of materials include woven fabrics, nonwoven fabrics, including needle punched nonwoven fabrics, hydro-entangled structures, chemically entangled structures, and other types of materials. Needle punched fabrics are particularly suitable if it is desirable to provide the tampon 26 with a textured outside surface.

One non-limiting example of a simplified manner of constructing the tampon 26 is as follows. In this example, the tampon 26 is made from materials similar to those currently used in conventional tampons. A rectangular web of absorbent material similar to that used to form a tampon pledget for conventional compressed tampons can be used as a starting material. This web of absorbent material can comprise a single layer of material such as a nonwoven web, or it can comprise more than one layer. It can be comprised of any of the types of materials described above. In a preferred embodiment, it comprises a 50%/50% blend of cotton and rayon fibers that is in the form of an airlaid nonwoven web. The web of absorbent material can be of any suitable thickness that is capable of being formed into a bag that is conformable as described herein. In such an embodiment, the web of absorbent material may, for example, be of a thickness that is equal to one of the layers of material that is typically formed into a tampon pledget. The web of absorbent material may, for example, be between about ¼ and about ½ (or more or less than) the thickness of a conventional tampon pledget that is formed from a plurality of such layers.

The web of absorbent material is then preferably covered with a single layer of nonwoven material of the type used to wrap conventional tampon pledgets. (In other embodiments, materials can be chosen for the tampon that do not require such an overwrap). If a nonwoven overwrap is used, the nonwoven material is preferably folded around the faces of the web of absorbent material. The nonwoven material is preferably of a sufficient size that it extends beyond the ends of the web of absorbent material. The portions of the nonwoven material that extend beyond the ends of the web of absorbent material are then preferably sealed together. The wrapped web of absorbent material is then folded about itself into a tube shape (or flattened tube shape) and sealed with a seam along one side and at one end to form the wrapped web of absorbent material into a bag structure. If desired, the bag can be turned inside out so the seams will be on the inside of the bag structure.

A key advantage of the tampon 26 described herein is that it can be provided with an absorbency that is considered to be "regular" absorbency (that is, about 6–9 grams of fluid) with only about one-half the amount of material that is used in conventional compressed tampons. This is attributable to, among other things, that the tampon 26 is flat like the vaginal cavity, and can be spread to fill the same, but need not be compressed in order to fit comfortably through the vaginal opening.

In a particularly preferred embodiment, the inside surface of the tampon 26 preferably has a different texture than the outside surface of the tampon 26. In particularly preferred embodiments, the tampon 26 is turned inside out for removal, and the inside surface has a smoother texture that provides improved comfort when the tampon 26 is removed and facilitates removal of the tampon 26. The inside surface of the tampon 26 can comprise a material that has a lower coefficient of friction against the wearer's body than the outside surface. The inside surface can also be provided with other features, such as a cleansing composition that can clean the wearer's vaginal area when the tampon 26 is removed.

The tampon 26 preferably has a removal string 44 that is attached thereto. The removal string 44 can be attached to the inside surface or the outside surface 40 of the tampon 26. In one particularly preferred tampon, the removal string 44 is attached to the inside surface of the tampon 26, adjacent to the head 26A of the tampon 26 to facilitate inversion of the tampon 26 upon removal.

The plunger 28 comprises a component that is used to expel the tampon 26 from its position within the holder 22 when the plunger 28 is pushed manually into the holder 22. The plunger 28 can be any type of component that is suitable for this purpose. Preferably, the plunger is telescopically and slidably mounted in the holder 22. The plunger 28 can be constructed similarly to plungers of the type used in tampon applicators currently in use. An example of a suitable plunger is described in U.S. Pat. No. 5,346,468 issued to Campion, et al. on Sep. 13, 1994, and U.S. Pat. No. 5,558,631 issued to Campion, et al. on Sep. 24, 1996.

In the embodiment shown in FIGS. 1–4 of the drawings, the plunger 28 comprises a tube which has its distal end (the end farthest from the expulsion end 22A of the holder 22) 28B formed into a gripping portion 50. As shown in FIGS. 1–4, the gripping portion 50 comprises a portion of the plunger 28 that is flattened and formed into a tab structure at the distal end 28B of the plunger 28. The tab comprises a planar extension of the distal end 28B of the plunger 28. The gripping portion 50 can serve several purposes, including serving as a positioning indicator, and to facilitate the retraction of the flexible loop 24 after the tampon 26 is deployed.

It should, however, be understood that the plunger 28 is not limited to a component having the configuration shown in the drawings, and that numerous other configurations may also be used. For example, instead of being formed into a gripping portion, the distal end 28B of the plunger 28 could be left unmodified as shown on the embodiment in FIGS. 5–8. In other alternative embodiments, the plunger 28 can be provided with an optional feature to allow the user to better grip the plunger 28. Suitable gripping features include raised formations, depressions, and apertures (similar to those structures which may be used as the finger grip 30 in the tubular holder 22).

It should also be understood that the plunger 28 is an optional, but preferred component for use with the present invention, and that the present invention will be fully functional if the plunger 28 is omitted, or if the plunger 28 comprises a part of the loop 24. Thus, the tubular plunger 28 shown in FIGS. 1–4 can omitted altogether, and the tampon 26 can be expelled when the user pushes on the ends 36 and 38 of the piece of material 34 that lie opposite the end of the piece of material 34 that is formed into the flexible loop 24.

To use the tampon applicator of the present invention the user will typically hold the holder 22 in one hand at the finger grips on the same. The holder 22 should be positioned adjacent to the vaginal opening with the indicator (if present) aligned so that when the tampon 26 is deployed, it will expand laterally within the wearer's vaginal cavity. The user holds the end of the plunger 28, such as with her thumb and forefinger, and pushes the plunger 28 inward to slide the plunger 28 within the holder 22. The user pushes on the plunger 28 until the loop 24 opens and the tampon 26 is deployed as shown in FIG. 3. The user then pulls the plunger 28 back outward in order retract the loop 24, and removes the applicator 20 from the vaginal opening.

The combination of the applicator 20 and the tampons described herein provides numerous advantages. One particular advantage is that the applicator 20 described herein is capable of applying a force to the inside of the leading end or "head" of the tampons of the type described herein. That is, it applies a force against the portion of the tampon that is oriented toward the wearer's cervix. This force preferably has a laterally outwardly-oriented vector component (more preferably, the applicators described herein provide two forces with outwardly-oriented vector components that are oriented in opposite directions) that act on the sides 26D of the tampon 26 adjacent to the leading end 26A. This will ensure that the tampon 26 is able to be expanded to a maximum width dimension at the head of the tampon 26. Thus, the applicator 20 of the present invention is able to fully deploy the bag-like tampons described herein, unlike prior spreading tampon applicators in which the greatest expansion occurs at some intermediate portion along the length of the applicator.

However, the present invention does not exclude embodiments of applicators (or tampons) in which the greatest expansion of the tampon occurs at intermediate portions thereof For instance, the applicators described herein can be configured to apply a force to a portion of inside surface of the tampon 26 that is midway (or half way) from the trailing end 26B of the tampon 26 to the head 26A of the tampon, or to some such portion of the tampon that lies between such a point and the head 26A of the tampon. In other embodiments, the applicators 20 can apply a force to a portion that is on the inside surface of the tampon 26 that is one third of the way from the trailing end 26B of the tampon 26 to the head 26A of the tampon, or to some such portion of the tampon that lies between a point which lies between such a point and the head 26A of the tampon.

In addition, alternative embodiments of the tampon 26 can be constructed which are configured so that the applicators described herein provide the greatest expansion at an intermediate portion of the tampon. For example, if the bag-like tampons described herein are provided with an insert (such as a small compressed batt of absorbent material (or small compressed tampon)) inside thereof at the head end 26A of the tampon 26, the applicators 20 described herein may press on the end of such a small compressed tampon rather than the head end of the bag-like structure. As a result, the greatest expansion may occur at some intermediate portion of the bag-like tampon. In still other embodiments, the applicators described herein can be used or modified to provide the greatest expansion at the trailing end of the tampon.

A non-limiting number of alternative embodiments of the present invention are also possible. In the form which is shown in FIGS. 1–4, the applicator 20 comprises a single loop of material 24.

FIGS. 5–8 show that in another embodiment, the flexible loop 24 can be provided with the ability to rotate as it deploys. Such an embodiment is useful in initially aligning the loop parallel to the opening of the vagina when the tampon is inserted through the vaginal opening, and then changing the orientation of the loop so that it is aligned parallel to the vaginal cavity when the tampon is deployed.

Figure 6:
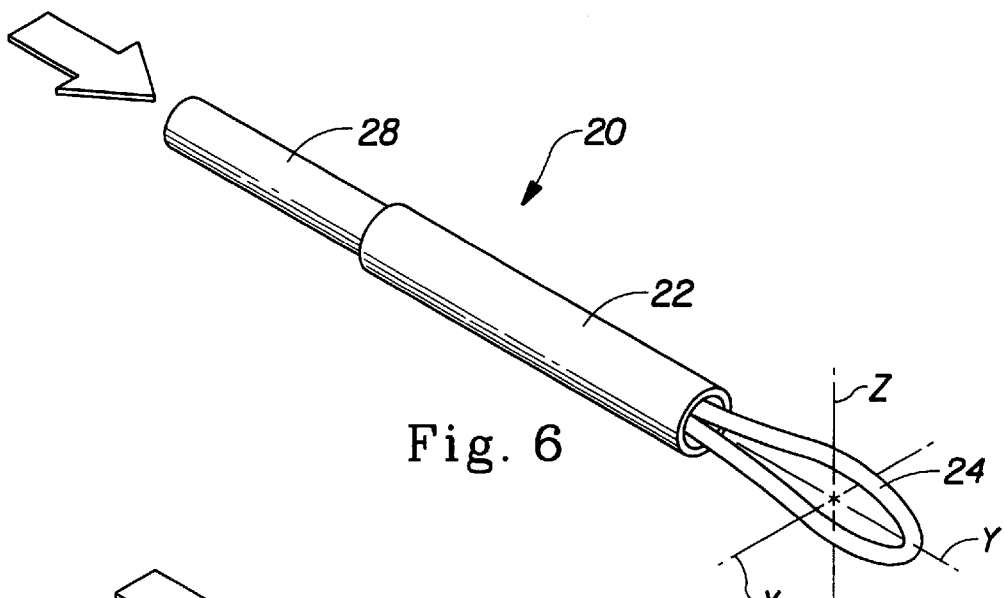
FIG. 6 is a perspective view of the tampon applicator shown in FIG. 5 which shows the flexible loop in a vertical position for insertion through the vaginal opening.
Figure 7:
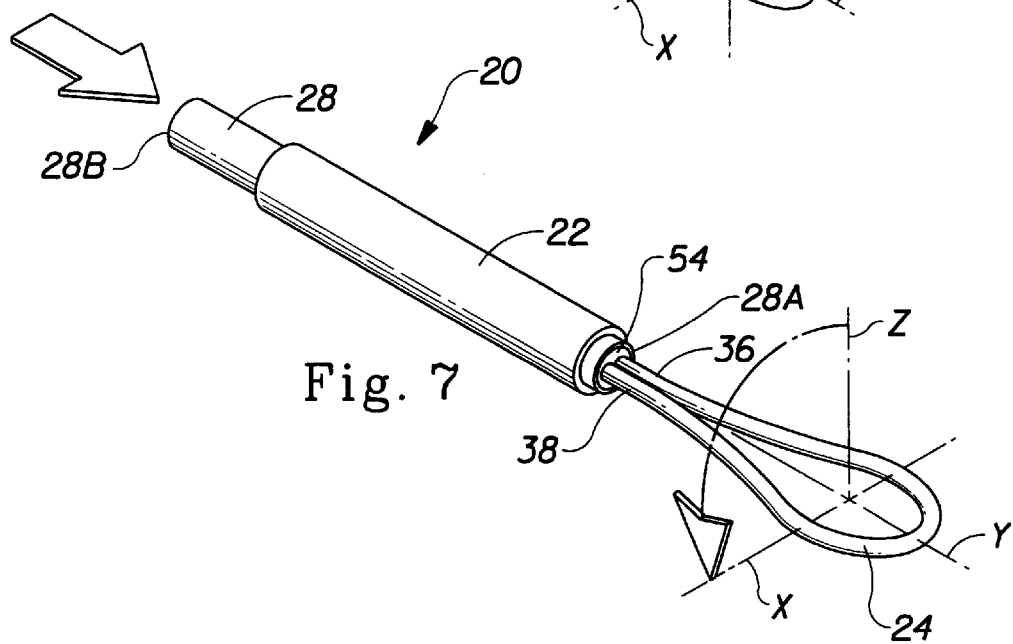
FIG. 7 is a perspective view of the tampon applicator shown in FIG. 5 which shows the flexible loop rotated 90 degrees for insertion of the tampon in the vaginal cavity.

The applicator shown in FIGS. 5–8 is simplified in that it is of an open end type, and it is not provided with finger grips, or the like. The plunger 28 of this embodiment, as shown in FIG. 7, has a leading end 28A and a distal end 28B. As shown in FIG. 7, the flexible loop 24 is preferably joined to the plunger 28. The term "joined", as used in this specification, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The flexible loop 24 can be joined to the plunger 28 in any suitable manner. In this particular embodiment, the ends 36 and 38 of the flexible loop 24 are embedded in a material, such as a plastic material 54 that fills the interior of the leading end 28A of the plunger 28.

It should be understood, however, that any of the embodiments of the applicators described herein can be provided with any of the features described herein, or combinations thereof, and that the embodiments shown are not limited to having the particular features shown in the drawings. The applicator shown in FIGS. 5–8 is also shown without the tampon thereon for simplicity of illustration.

FIG. 5 shows the applicator 20 as the flexible loop 24 is just beginning to be deployed. FIG. 6 shows the flexible loop 24 as it is partially deployed before it rotates. As shown in FIG. 6, the flexible loop 24 is in a vertical position that matches the orientation of the vaginal opening. That is, the flexible loop 24 lies in the Y-Z plane. FIG. 7 shows the applicator 20 when the flexible loop 24 is fully deployed and rotated 90 degrees from the position shown in FIGS. 5 and 6 to correspond to the orientation of the vaginal cavity. That is, the loop lies in the X-Y plane.

Figure 8:
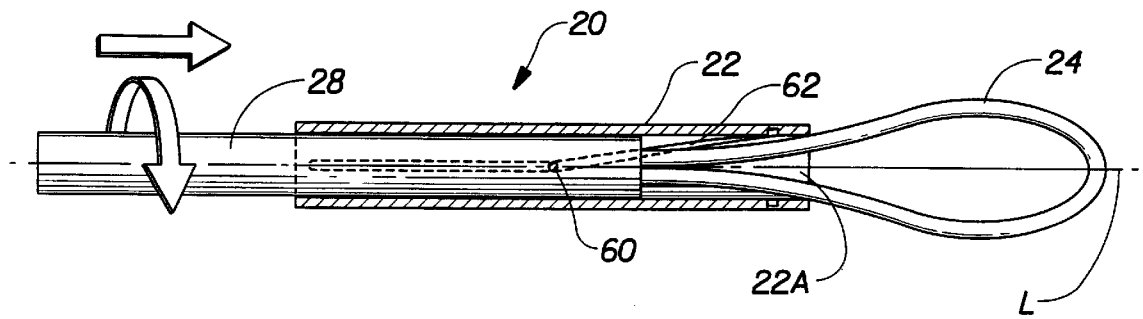
FIG. 8 is a side view of the tampon applicator shown in FIG. 5, partially cut away, which shows the mechanism which provides the flexible loop with the ability to rotate.

FIG. 8 shows one preferred mechanism used to make the flexible loop 24 rotate. As shown in FIG. 8, a pin 60 passes through at least one of the components of the applicator that slides through the holder 22. The pin 60 is preferably connected either directly or indirectly to the flexible loop 24. The ends of the pin 60 engage with a pair of channels 62 on the inside surface of the tubular holder 22. The channels 62 are preferably initially oriented parallel to the longitudinal centerline, L, of the holder 22. This is shown as the portions of the channels 62 that lie to the left of the pin 60 in FIG. 8. The channels 62 then angle away from the longitudinal centerline of the holder 22 toward the expulsion end 22A of the holder 22. When the pin 60 slides through the channels 62, this angling away of the channels 62 toward the expulsion end 22A causes the flexible loop 24 to rotate.

The embodiment shown in FIGS. 5–8 is preferably intended to be capable of only operating properly when the user inserts the tampon in the proper orientation. This will automatically correctly spread the tampon laterally across the width of the vaginal cavity. The embodiment shown in FIGS. 5–8, once it is in the proper insertion orientation, thereby provides a "signal" to the user that the tampon is properly deployed.

Figure 9:
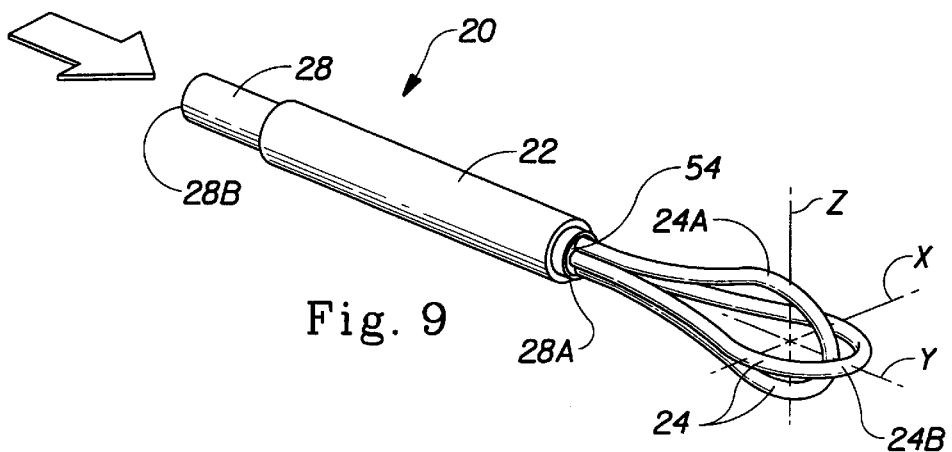
FIG. 9 is a perspective view of a preferred alternative embodiment of the tampon applicator of the present invention which comprises two flexible loops that are oriented at a 90 degree angle relative to each other.
Figure 10:
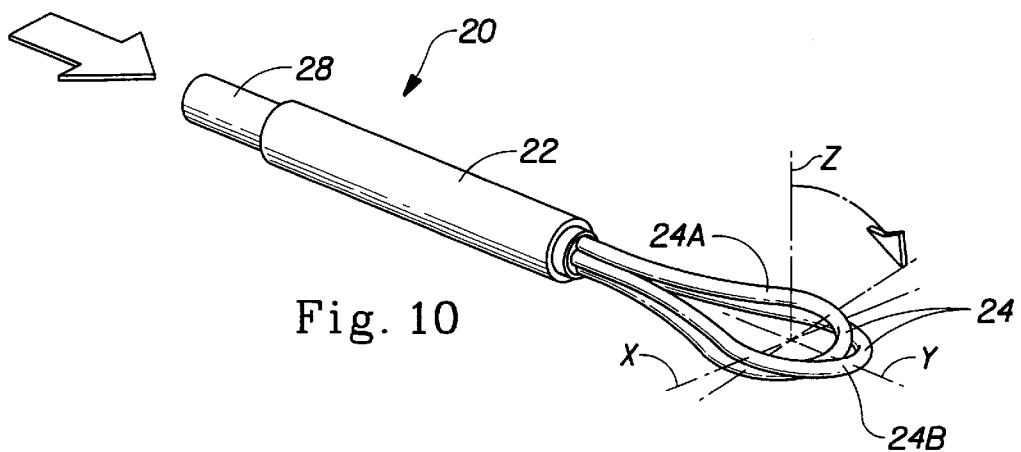
FIG. 10 is a perspective view of the tampon applicator shown in FIG. 9 which shows how the two loops will come together to a similar planar relationship to accommodate the shape of the vaginal cavity.

In another embodiment, a particularly preferred embodiment, which is shown in FIGS. 9 and 10, the applicator comprises two (or more) loops of material. The loops of material 24 can be oriented in any suitable relationship relative to each other. In this particularly preferred embodiment, the loops of material 24A and 24B are preferably oriented at an angle of about 90 degrees relative to each other when the applicator 20 is viewed from the end. This embodiment has the advantage of providing an increased likelihood of ensuring that at least one of the loops of material will be oriented in the same plane as the vaginal cavity regardless of the orientation of the applicator 20 when it is inserted in the vaginal cavity. As shown in FIG. 10, even though the loops 24A and 24B were initially oriented at right angles, they are sufficiently flexible under low forces that one of the loops (in this case 24A) will be capable of "flattening" and adjusting its orientation to that of the other loop. This allows it to conform to the collapsed orientation of the vaginal cavity. The embodiment shown in FIGS. 9 and 10 is capable of adjusting in this manner regardless of how the loops are initially oriented relative to the vaginal cavity. As a result, there is no need for the user to be concerned with properly orienting the applicator 20 relative to the vaginal opening.

Figure 11:
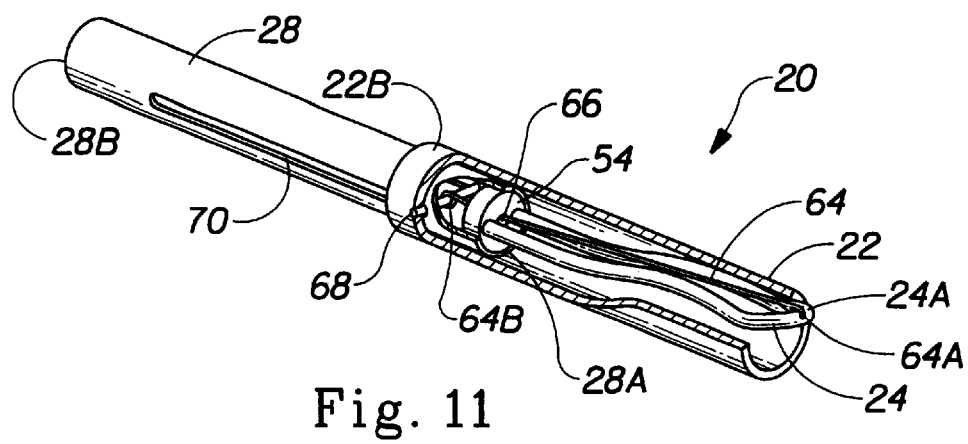
FIG. 11 is a partially fragmented perspective view of another alternative embodiment of the tampon applicator of the present invention in which the flexible loop is constrained in length as it deploys by having a portion thereof joined to the holder.
Figure 12:
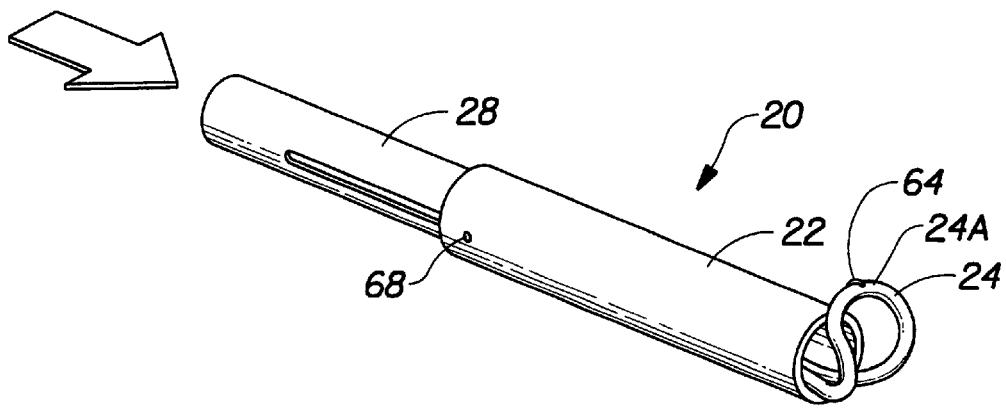
FIG. 12 is a perspective view of the tampon applicator shown in FIG. 11 in a partially deployed condition.
Figure 13:
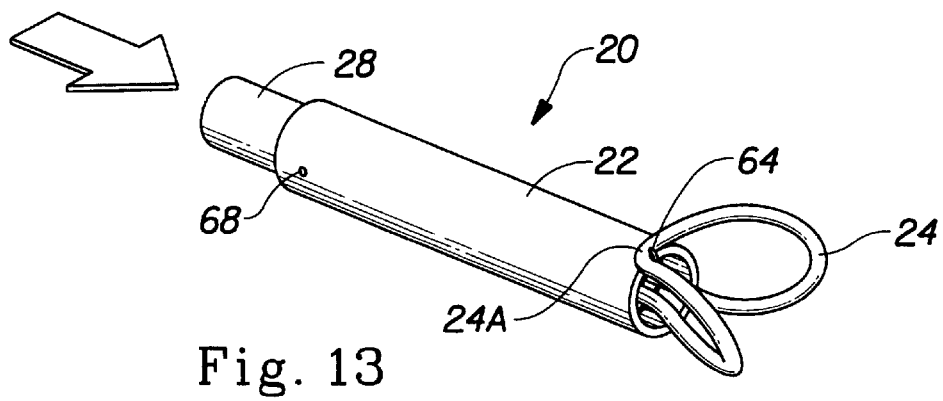
FIG. 13 is a perspective view of the tampon applicator shown in FIG. 11 in a fully deployed condition.

FIGS. 11–13 show that in another embodiment, the applicator 20 has a loop 24 that is constrained in length as it deploys. This provides the loop 24 with the desired transverse spreading action, but is in the form of a structure that has a shorter length when deployed. The constrained loop 24 in this embodiment may also provide a greater spread in the transverse direction (that is, in width) in comparison to the types of loops shown in the preceding figures.

In FIGS. 11–13, the loop 24 is preferably constrained in length by joining a portion of the loop 24 to another portion of the applicator 20. More specifically, in this embodiment the leading end 24A of the loop 24 is joined by an element, such as a string 64 that has one end 64A joined to the leading end 24A of the loop 24 and its opposite end 24B joined to a portion of the applicator, such as the holder 22. Preferably, in this embodiment, the end 24B of the string 24 passes through a hole 66 in the material 54 in which the ends of the flexible loop 24 are embedded. In the embodiment shown, the end of the string is joined to a pin 68 (which can be similar to the pin used in the previous embodiment) that passes through the holder 22. The plunger 28 has a pair of channels 70 therein that accommodate the pin 68 when the plunger 28 is pushed into the holder 22. The pin 68 and the end of string 64B attached thereto remain fixed in position, and the string 64. Since the string 64 is of a constant length, this maintains the leading end 24A of the loop in the same relative position before and after the flexible loop 24 is deployed. As shown in FIGS. 12 and 13, when deployed, the loop 24 in this embodiment resembles a "ram's horn" in appearance.

Figure 14:
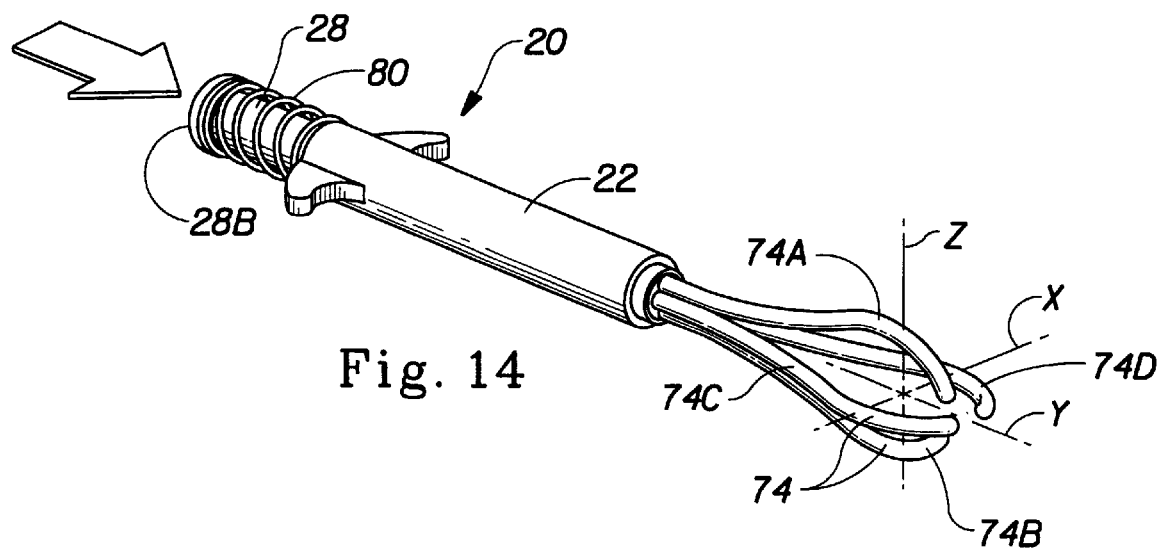
FIG. 14 is a perspective view of another alternative tampon applicator which comprises several flexible prongs instead of a flexible loop.

FIG. 14 shows another alternative embodiment of the present invention in which the loop has been replaced with several prongs 74, which serve as the applicator element(s). In the embodiment shown in FIG. 14, there are four prongs 74A, B, C, and D that resemble the loops of the embodiment shown in FIGS. 9 and 10 in their arrangement relative to each other. This embodiment is an example of a flexible, movable structure that comprises one or more elements, the prongs 74. The prongs 74 are preferably convexly rounded to provide a comfortable surface against the wearer's body. The prongs 74 are preferably arranged in pairs, each having two opposing prongs 74 that are capable of flexing and expanding away from each other.

Figure 15:
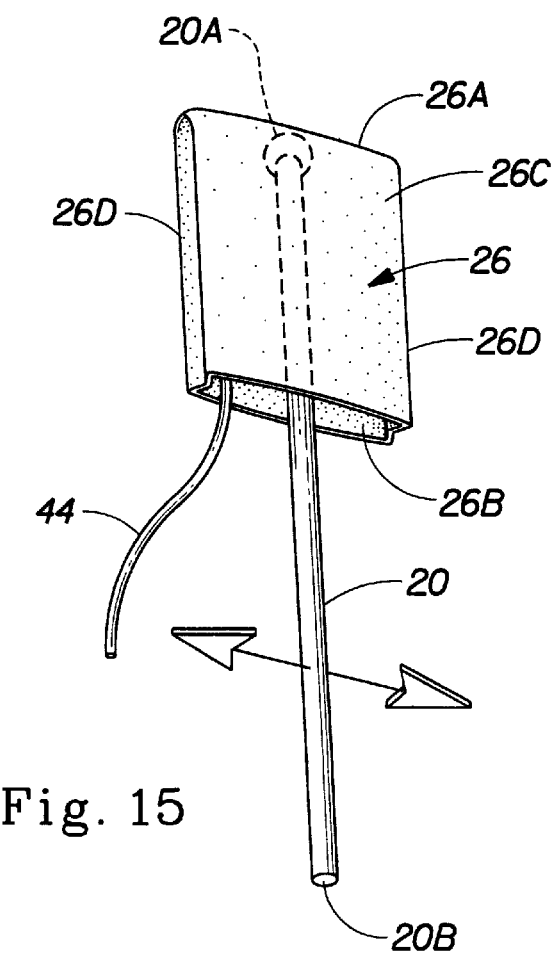
FIG. 15 is a perspective view of a simplified version of a tampon applicator and a tampon that it may be used to spread open by manually moving the applicator from side to side.

Numerous other embodiments and features can be provided. For example, as shown in FIG. 15, the spreading tampon applicator 20, in one simple, albeit less convenient embodiment, can comprise a member such as a simple rigid or semi-rigid rod or tube that is used in conjunction with the hollow, bag-like tampon 26. The rod 20 has a leading end (or distal end) 20A for insertion into portion of the tampon that will first enter the wearer's vagina and a trailing end (or proximal end, since it is closest to the wearer's hand during insertion) 20B that the user holds.

The type of applicator 20 shown in FIG. 15 is not limited to structures in the nature of rods or tubes, however. Such an applicator can be of many suitable shapes. For instance, the applicator 20 can be formed by flattening a cylindrical cardboard applicator of a conventional type, and binding the applicator so that it remains in a flattened condition. Alternatively, the applicator 20 can resemble an analytical spatula. The applicator 20 may have a portion adjacent to the leading end 20A that is spoon-shaped (or "shoe horn" shaped) to fit the wearer's cervix. In other embodiments, the portion of the applicator 20 that is adjacent to the leading end 20A (for example, the distal half of the applicator) can comprise a structure in the nature of a flattened stick. This portion of the applicator may resemble a tongue depressor.

Regardless of the configuration of such an applicator, the leading end 20A is preferably rounded or soft so that it is comfortable for the user. The leading end 20A can be provided in a rounded configuration, or with soft properties in many suitable ways. The leading end 20A can, for example, comprise a ball-like element, a bulbous projection, or a circular or semi-circular element. In these or other embodiments, the leading end 20A of the rod 20 can comprise a compressible material, or a soft material, which may include, but is not limited to a compressed foam. Further, if it is desired to provide a more compact applicator of the type shown in FIG. 15, the applicator can comprise one or more telescoping pieces and a locking mechanism for locking the pieces in an extended configuration.

The hollow, bag-like tampon 26 is fit over the rod 20 and the tampon 26 is inserted into the vagina by pressing against the inside surface of the tampon adjacent to the "head" (or leading end) 26A of the tampon 26. The tampon 26 has an initial width when it is fit over the applicator 20. The user can then expand the tampon to a greater deployed width. Preferably, the user spreads the longitudinal sides 26D of the tampon 26 in some suitable manner so that the tampon 26 is spread across the width of the vagina. In the simplest embodiment, the user moves the rod 20 side to side manually until the tampon 26 is spread to the desired condition.

As noted above, the applicator 20 may optionally be provided with a positioning indicator for assuring that the tampon is deployed properly in the vaginal cavity. The positioning indicator can be any suitable type of element that assures that the tampon is properly deployed. Suitable positioning indicators include, but are not limited to: a discontinuity on one or more portions of the applicator 20 or difference in the shape of one or more portions of the applicator 20 (such as a flattened portion of the same); indicia such as a mark on one or more portions of the applicator 20, or combinations of any of the foregoing. If a positioning indicator is used, it is preferably sensitive to touch to enable the user to properly position the applicator for insertion of the tampon without the necessity of viewing the indicator to ensure proper insertion. In the embodiment shown in FIGS. 1–4, the gripping portion 50 on the trailing end 28B of the plunger 28 can serve as the positioning indicator. Preferably, however, the applicator 20 is one which can be used regardless of how it is initially oriented, and is of a type that does not require a positioning indicator.

In addition, as shown in FIG. 14, the applicator 20 may be spring-loaded, such as by providing it with a spring 80 near the trailing end 28B of the plunger 28 (or on some other element of the applicator) that biases the plunger 28 toward a retracted position. Thus, when the user pushes on the plunger 28 to deploy the tampon, the spring 80 will be compressed. The spring 80 will exert a force which will tend to make the plunger 28 return toward the retracted position. After the user stops pushing on the plunger 28, the plunger 28 will automatically return to its retracted condition with no action required on the part of the user.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

While particular embodiments of the present invention have been illustrated and described, it would be obvious to those skilled in the art that various other changes and modifications can be made without departing from the spirit and scope of the invention.

What is claimed is:

1. A combination of a catamenial tampon applicator and a tampon, said combination comprising:

an applicator comprising an applicator element with an expandable leading end and a trailing end; and a tampon having a bag structure having an open trailing end and a closed head end, said tampon having a flaccid initial configuration which defines an initial width, and a spread deployed configuration which defines a greater deployed width, wherein said open trailing end of said tampon fits over at least a portion of the leading end of said applicator element.

2. The combination of claim 1 wherein said tampon has an inside surface, and an outside surface, and wherein said applicator element when expanded is configured to contact the inside surface of said tampon along the closed head end of the tampon.

3. A combination of a catamenial tampon applicator and a tampon, said combination comprising:

an applicator comprising an applicator element with a leading end and a trailing end wherein said applicator element comprises at least one laterally expandable structure; and a tampon having a bag structure, said tampon having a flaccid initial configuration which defines an initial width, and a spread deployed configuration which defines a greater deployed width, wherein said tampon fits over at least a portion of the leading end of said applicator element.

4. The combination of claim 3 wherein said applicator element comprises at least one flexible loop of material.

5. The combination of claim 3 wherein said applicator element comprises at least one pair of opposed prongs.

6. A combination of a catamenial tampon applicator and a tampon, said applicator comprising an expandable applicator element having a distal end capable of being inserted into a user's vagina and a proximal end, said tampon having a bag structure with an initial width and a deployed width and an open end and a closed end, said open end of said bag structure fitting over at least a portion of said applicator element, and said applicator element having means that allows said user to expand said tampon so that its deployed width is greater than its initial width.

7. The combination of claim 6 wherein said tampon has an inside surface, an outside surface, and sides, wherein said applicator element is configured to contact the inside surface of said tampon along the closed end of the tampon, the applicator element being capable of applying forces having a laterally outwardly-oriented vector component to the inside surface of the tampon proximate its closed end to expand the sides of the tampon adjacent to the closed end of the tampon.

* * * * *